(12) United States Patent
Rührnschopf et al.

(10) Patent No.: US 7,782,996 B2
(45) Date of Patent: Aug. 24, 2010

(54) METHOD FOR COMBINED BONE HARDENING AND SCATTERED RADIATION CORRECTION IN X-RAY COMPUTED TOMOGRAPHY

(75) Inventors: Ernst-Peter Rührnschopf, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 325 days.

(21) Appl. No.: 11/903,800

(22) Filed: Sep. 25, 2007

(65) Prior Publication Data

US 2008/0159469 A1    Jul. 3, 2008

(30) Foreign Application Priority Data

Sep. 28, 2006 (DE) .................. 10 2006 046 047

(51) Int. Cl.
   *A61B 6/00* (2006.01)
(52) U.S. Cl. ............................................. 378/4
(58) Field of Classification Search ................ 378/4, 378/7
   See application file for complete search history.

(56) References Cited

U.S. PATENT DOCUMENTS

| | | | | |
|---|---|---|---|---|
| 5,438,602 | A * | 8/1995 | Crawford et al. | 378/4 |
| 5,953,444 | A * | 9/1999 | Joseph et al. | 382/131 |
| 6,507,633 | B1 * | 1/2003 | Elbakri et al. | 378/8 |
| 6,879,715 | B2 * | 4/2005 | Edic et al. | 382/132 |
| 2005/0105693 | A1 * | 5/2005 | Zhao et al. | 378/210 |
| 2005/0249431 | A1 * | 11/2005 | Ruhmschopf | 382/274 |
| 2006/0067461 | A1 * | 3/2006 | Yin et al. | 378/5 |
| 2007/0104310 | A1 * | 5/2007 | Nottling et al. | 378/4 |

OTHER PUBLICATIONS

Peter M. Joseph and Robin D. Spital, "A Method for Correcting Bone Induced Artifacts in Computed Tomography Scanners", Journal of Computer Assisted Tomography, Jan. 1978, pp. 100-108, vol. 2, No. 1, Raven Press, New York.
Peter M. Joseph and Robin D. Spital, "A Method for Simultaneous Correction of Spectrum Hardening Artifacts in CT Images Containing both Bone and Iodine", Medical Physics, Oct. 1997, pp. 1629-1634, vol. 24, No. 10.
M. Zellerhoff, B. Scholz, E.-P.Rührnschopf and T. Brunner, "Low Contrast 3D-Reconstruction from C-Arm Data", Proceedings of SPIE, Medical Imaging 2005, pp. 646-665, vol. 5745.
Yiannis Kyriako, Thomas Riedel and Willi A Kalender, Combining Deterministic and Monte Carlo Calculations for Fast Estimation of Scatter Intensities in CT, Physics in Medicine and Biology, 2006, pp. 4567-4586, vol. 51, IOP Publishing Ltd, UK.
Dr. Hans-Joachim Kowalsky, "Lineare Algebra", 1972, pp. 22-27, Walter de Gruyter, Berlin, New York, 1972.

* cited by examiner

*Primary Examiner*—Edward J Glick
*Assistant Examiner*—Alexander H Taningco

(57) ABSTRACT

The invention relates to a method for combined bone hardening and scattered radiation correction in X-ray computed tomography of a heterogeneous object with a CT system comprising an X-ray source moved around an object, a flat detector with a large number of distributed detector elements which detect measuring beams from a focal point of the X-ray tube, and a control and arithmetic-logic unit—by iterative reconstruction and segmented vectorial reprojection calculation, wherein a scattered radiation correction and a radiation hardening correction are carried out in each iteration cycle for at least two different material components of the object being examined. The invention also relates to an X-ray CT system for carrying out this method.

11 Claims, 3 Drawing Sheets

METHOD FOR COMBINED BONE HARDENING AND SCATTERED RADIATION CORRECTION IN X-RAY COMPUTED TOMOGRAPHY

CROSS REFERENCE TO RELATED APPLICATIONS

This application claims priority of German application No. 10 2006 046 047.2 filed Sep. 28, 2006, which is incorporated by reference herein in its entirety.

FIELD OF THE INVENTION

The invention relates to a method for combined bone hardening and scattered radiation correction in X-ray computed tomography (CT) of a heterogeneous object with a CT system, comprising an X-ray source moved around an object, a flat detector with a large number of distributed detector elements which detect measuring beams from a focal point of the X-ray tube, and a control and arithmetic-logic unit. The invention also relates to a CT system which is capable of carrying out such a method.

BACKGROUND OF THE INVENTION

Owing to the large solid angle that is captured, scattered radiation plays a significant part in computed tomography with multi-line and flat panel detectors. Even if anti-scatter grids or special collimators are used to reduce the scattered radiation the intensity thereof can still be considerable and even exceed the primary intensity. Artifacts consequently result as well as quantitative falsifications following image reconstruction, with errors in excess of 100 HU (=Hounsfield units). Additional scattered radiation correction methods are therefore required.

Spectral radiation hardening effects also occur in principle in the case of CT with X-ray tubes which emit a polychromatic photon spectrum. These effects manifest themselves following image reconstruction as what are known as "cupping", i.e. trough-like density reduction from the outside in, even with homogeneous material, such as water in a cylinder. Image errors of up to >100 HU which, for example, occur as bar-like artifacts between prominent bone structures result in this case as well. In terms of appearance the falsifications generated by hardening or scattered radiation are very similar and it is almost impossible to differentiate them.

It is known that the presence of bones in the beam path affects hardening and scattered radiation, albeit differently. With radiologically different materials, such as soft tissue and bone, the scattered radiation depends not only on the fractions of the two materials but also on their sequence in the beam path. This means that the scattered radiation intensity can for example be significantly different with the same primary attenuation and with a combination of water and bone if exactly opposing projections, for example anterior→posterior and posterior→anterior, are examined. Hardening on the other hand is independent of the sequence of materials.

Post-reconstructive iterative hardening correction algorithms that take account of bone have already been published a long time ago. In this case reference is made by way of example to the documents P. Joseph, R. Spital: "A Method for Correcting Bone Induced Artifacts in Computed Tomography Scanners", J. Comp. Assist. Tomogr., January 1978, vol. 2, pp. 100 to 108 and P. Joseph, C. Ruth, "A Method for Simultaneous Correction of Spectrum Hardening Artifacts in CT Images Containing Both Bone and Iodine", Med. Phys. vol. 24 (10), October 1997, pp. 1629 to 1634.

From the document M. Zellerhof, B. Scholz, E.-P. Ruhrnschopf, T. Brunner: "Low contrast 3D reconstruction from C-arm data", Proceedings of SPIE. Medical Imaging 2005, vol. 5745, pp. 646 to 655 a hardening correction of CT projection data is also known as pre-reconstructive "water correction" in which in simplistic terms it is assumed that the attenuation of the X-radiation is caused solely by water-equivalent material. The pre-reconstructive scattered radiation correction method that is also outlined therein is based on similar simplified assumptions.

SUMMARY OF THE INVENTION

It is therefore the object of the invention to present a correction method for CT projection data that is improved compared with the prior art and which better compensates the actually occurring scattered radiation and radiation hardening during examination of an object.

This object is achieved by the features of the independent claims. Advantageous developments of the invention are the subject matter of subordinate claims.

The inventors recognized the following:

The superposition of hardening and scattered radiation leads to recursive systems of equations in the case of correction methods: on the one hand the hardening correction requires scattered radiation correction and on the other hand estimation of the scattered radiation requires information such as the primary intensity distribution of the radiation used and the material coverage thicknesses of the object being examined, which are actually only available following correction.

Reflexive problems may be dealt with using the mathematical methods of iteration. An iterative method of this kind should take account of the above-described interlacing of scattered radiation and hardening within the framework of a post-reconstructive correction.

To take account of the internal structures of the object being examined, for example of bone in a patient, knowledge of the share of bone material in each measuring beam, i.e. for the projection measured value in the detector pixel, is required. This knowledge can be approximately obtained by a segmented reprojection along each measuring beam through a volume that has already been reconstructed by means of a three-dimensional reconstruction algorithm. The segmented reprojection provides the material coverage of different material components for each measuring beam, for example of water-equivalent material and of bones, which the measuring beam has penetrated.

The inventive method will be described hereinafter using the example of a two-component distinction, in this case soft tissue and bone, wherein this should not be regarded as a limitation of the invention. In generalized terms the same method may also be easily transferred to a large number of different components.

The two-component hardening correction consists in the conversion of the non-linear polychromatic measured value into an ideal linear monochromatic measured value.

A plurality of method steps which in practice can be stored in the form of mathematical programs or sub-programs in a data processing system of a CT device, form part of the proposed method.

The Three-Dimensional CT Reconstruction:

Basically any known reconstruction method can be used here which provides volumetric data of the object being examined from a large number of projection data of a CT examination. Formally this operation is hereinafter designated by $$f=B(g),$$

wherein g denotes logarithmic projection measuring data, generally a series of two-dimensional CT projection images for a large number of projection directions which are taken approximately on a circle, at least a semi-circle plus cone opening angle, around the patient, and f a reconstructed "volumetric image", i.e. a voxel representation of the object being imaged.

Segmented, Vectorized Reprojection:

For this purpose a reconstructed volumetric image f is given. Using a reprojection algorithm which numerically simulates the image geometry, measuring data can again be artificially calculated from a "voxeled" volumetric image. Each measuring beam can be separated into different, in this case, two, attenuation fractions, namely into a fraction which is attenuated by soft tissue and a fraction which is attenuated by bone substance, by the segmented reprojection, for example by using a threshold criterion. These fractions may be determined as scalar surface coverage densities $b_w$ [g/cm$^2$] for the soft tissue and $b_K$ (g/cm$^2$) for the bone tissue, knowledge of which is sufficient for two-component hardening correction.

The vectorized reprojection includes additional information about the sequence of soft tissue and bone fractions along a measuring beam which are required for a two-component scattered radiation correction. The product of path length and density, i.e. the local surface coverage per voxel, can also be stored for each voxel in the case of this reprojection for soft tissue and bone in a vector $\underline{\lambda}$. A triple ($b_w$, $b_K$, $\underline{\lambda}$) is thus determined for each measuring beam by a segmented vectorial reprojection of this kind and can be used for the subsequent two-component scattered radiation correction or hardening correction.

Symbolically this calculation is described by:

$$(b_W, b_K; \lambda) = \underline{R}(f).$$

Two-Component Hardening Correction:
This correction is formally described by:

$$g = H(\tilde{g}; b_W, b_K)$$

wherein:

$\tilde{g}$ denotes polychromatically measured logarithmic projection value, $b_w$ denotes soft tissue coverage density [g/cm$^2$] integrated along the measuring beam, $b_K$ denotes bone coverage density [g/cm$^2$] integrated along the measuring beam, g denotes hardening-corrected projection value, converted to monochromatic radiation.

Scattered Radiation Correction:
This includes two sub-items, namely:

a) a scattered radiation estimation model: in this case the local scattered radiation distribution S(x,y) is estimated from a predefined local primary intensity distribution P(x,y) on the detector surface. In this case it is not only the conventional image parameters: tube potential, pre-filtering, detector material, air gap, collimated detector field size and scattered radiation grid that have to be considered, but also (and it is this that, in the inventors' view, constitutes the fundamental difference from the prior art) at least approximately, the quantity and sequence of different material components in the beam path, in this case of water-equivalent soft tissue and bone. This is described by:

$$S(x,y) = S_{estim}(P; b_W, b_K, \underline{\lambda})(x,y).$$

Wherein:

(x,y) denotes the coordinates of the detector pixel or the measuring beam of the radiation source, i.e. from the focal point of the X-ray tube to the detector pixel, P(x,y) denotes the standardized primary intensity distribution over the detector, $b_w$ for each pixel (x,y) denotes the coverage density totaled along the measuring beam for soft tissue; results from segmented reprojection respectively, $b_K$ for each pixel (x,y) denotes the coverage density totaled along the measuring beam for bone; results from segmented reprojection respectively, $\underline{\lambda}$ denotes a vector, in the simplest case a scalar parameter, which describes the distribution or sequence of bone and soft tissue along the measuring beam, $S_{estim}$ denotes the estimation procedure which also depends on acquisition parameters, such as scatted radiation grid, air gap, potential and detector field size, the subscript "estim" should point to the fact that it is an arithmetic model with which the scattered radiation is to be estimated (estimation).

An extension of the "folding model" from the document M. Zellerhof, B. Scholz, E.-P Rührnschopf, T. Brunner: "Low contrast 3D reconstruction from C-arm data", Proceedings of SPE. Medical Imaging 2005, vol. 5745, page 646 to 655, can be used by way of example as the estimation procedure.

b) a scattered radiation correction algorithm: using the scattered radiation correction algorithm a predefined intensity distribution $$\tilde{P}(x,y),$$

which should be interpreted as an overlaying of primary and scattered radiation is corrected with a given (estimated) scattered intensity distribution S(x,y) such that a primary intensity distribution P(x,y) is, at least approximately, obtained therefrom. A correction procedure of this kind is designated by:

$$S_{corr}(\tilde{P}; S).$$

The actual iteration method is described on the basis of the above-described method steps or algorithms. Iteration algorithms formally comprise three parts: the start of iteration with the definition of the initial values, the iteration loop and the termination condition. Omitting the pixel coordinates, these are as follows in this case:

I) Start of Iteration:

1) initial estimation for standardized primary distribution for each projection angle α where:

$$P^{(0)} = I/I_0$$

2) initial estimation for a logarithmic projection image for each projection angle α:

$$g^{(0)} = -\ln(P^{(0)})$$

3) initial image from a CT volume reconstruction using image reconstruction algorithm B $$f^{(0)} = B(g^{(0)})$$

II) Iteration Loop:

The iteration rule determines the transition from the iteration number n (n≧0) to the next iteration number n+1. It should be noted that—irrespective of the three-dimensional CT reconstruction—two-dimensional functions exist over the detector surface for each projection angle. The following steps are carried out in the iteration loop:

1) Segmented vectorized reprojection for each measuring beam between focal point and detector pixel (x,y) where:

$$(b_W^{(n)}, b_K^{(n)}; \underline{\lambda}^{(n)}) = \underline{\mathscr{R}}(f^{(n)})$$

2) Two-component scattered radiation estimation method where:

$$S^{(n)} = \mathscr{O}_{\bullet \bullet \bullet}(P_E^{(n)}; b_K^{(n)}; \underline{\lambda}^{(n)})$$

3) Scattered radiation correction and new estimation of the primary radiation distribution $$P^{(n+1)} = S_{corr}(P^{(n)}; S^{(n)})$$

4) Calculation of scattered radiation-corrected projection images from the logarithmization of the primary radiation distribution:

$$\tilde{g}^{(n+1)} = -\ln(P^{(n+1)})$$

5) Component hardening correction $$g^{(n+1)} = I(\tilde{g}^{(n+1)}; b_W^{(n)}, b_K^{(n)})$$

6) Three-dimensional CT reconstruction $$f^{(n+1)} = B(g^{(n+1)})$$

III) Termination of Iteration

The iteration sequence can be terminated for example if the change between successive iterations is less than a low threshold that is to be predefined or a specific number of iterations have been undergone. In most cases, in particular with a relatively small to moderate scatter fraction, one iteration cycle, i.e. passing through the iteration loop twice, can suffice.

In the inventors' view an optimum development of the method contains the following method steps:

start of iteration by:
determining a first standardized radiation distribution $P^{(0)}$ of the radiation striking the detector for a large number of projection angles,
calculating a projection image $g^{(0)}$ from the first logarithmized radiation distribution for a large number of projection angles,
reconstructing a first tomographic volumetric image $f^{(0)}$, iteration loop:
segmenting the last-ascertained volumetric image $f^{(n)}$ into m components and determining the distribution of the m material components on each measuring beam,
estimating a scattered radiation (intensity) distribution by taking account of the distribution of the material components on all measuring beams,
correcting the last-ascertained radiation distributions using this scattered radiation correction to give improved radiation distributions $P^{(n+1)}$,
calculation improves scattered radiation-corrected projection images $g^{\sim(n+1)}$,
estimating a hardening correction by taking account of the fraction of material components penetrated per measuring beam,
correcting the improved radiation-corrected projection images $g^{\sim(n+1)}$ by the last-ascertained hardening correction to give improved radiation- and hardening-corrected projection images $g^{(n+1)}$,
reconstructing an improved radiation- and hardening-corrected tomographic image $f^{(n+1)}$, iterative branching by:
ascertaining at least one predefined iteration condition and terminating or continuing the iteration loop depending on the result of the ascertained iteration condition.

An alternative variant to this method which optionally requires slightly more iteration loops to achieve an adequate result can lie in the sequence of scattered radiation correction and hardening correction being transposed. The following method steps thus result:

start of iteration by:
determining a first standardized radiation distribution $P^{(0)}$ of the radiation striking the detector for a large number of projection angles,
calculating a projection image $g^{(0)}$ from the first logarithmized radiation distribution for a large number of projection angles,
reconstructing a first tomographic volumetric image $f^{(0)}$, iteration loop:
segmenting the last-ascertained volumetric image $f^{(n)}$ into m components and determining the distribution of the m material components on each measuring beam,
estimating a hardening correction by taking account of the fraction of material components penetrated per measuring beam,
correction of the last-obtained projection images $g^{\sim(n+1)}$ by the last-ascertained hardening correction to give improved hardening-corrected projection images $g^{(n+1)}$,
estimating a scattered radiation correction by taking account of the distribution of the material components on all measuring beams,
correcting the hardening-corrected projection images using this scattered radiation correction to give improved hardening-corrected radiation distributions $P^{(n+1)}$,
calculation improves scattered radiation-corrected projection images $g^{\sim(n+1)}$,
reconstructing an improved radiation- and hardening-corrected tomographic image $f^{(n+1)}$, iterative branching by:
ascertaining at least one predefined iteration condition and terminating or continuing the iteration loop depending on the result of the ascertained iteration condition.

In a specific case of examination of a patient with limited arithmetic capacity the number of material components can be limited to m=2, it being advantageous to use soft tissue as the first material component and bone tissue as the second material component.

An improvement in this variant can be achieved if m=3 material components are used, it being particularly advantageous if air is used as the first material component, soft tissue is used as the second material component and bone tissue as the third material component. Significantly better results can be obtained herefrom in particular with an examination in the air-containing thorax region. For m=3, soft tissue, bone and contrast medium or for m=4, air, soft tissue, bone and contrast medium are cited as further preferred material combinations.

In a manner similar to the above-described method the inventors also propose an X-ray CT system for tomographic imaging of an object to be examined, comprising an X-ray source, a flat detector and an arithmetic-logic unit in which a reconstruction of volumetric data of the object is carried out from the detector data output by the detector during the examination, computer programs being stored for this purpose in the memory of the arithmetic-logic unit and the memory of the arithmetic-logic unit also containing computer programs during the execution of which an inventive method as described above is carried out.

The inventive method and the inventive CT system in particular provide the following advantages:

The quantitive accuracy of the CT reconstruction, i.e. the accuracy in HU units, may be increased by the iteration cycle, including scattered radiation correction.

The image artifacts, for example "Hounsfield bars" between bones, caused by radiation hardening and similarly by scattered radiation are significantly reduced.

An improvement in the scattered radiation correction is made possible by the iterative inclusion in that the scattered radiation estimation model can be refined using the additional information about the coverage thicknesses of the material components—which would not be available without iteration.

The clear mathematical formalization allows a simple generalization to a calculation with a large number of different material components.

In accordance with these considerations the inventors propose an improvement in a scattered radiation and beam hardening correction in CT imaging of a heterogeneous object using a CT system, comprising an X-ray source that is moved around an object, a flat detector with a large number of distributed detector elements which detect measuring beams from a focal point of the X-ray tube, and a control and arithmetic-logic unit, according to which a combined bone hardening and scattered radiation correction takes place by way of iterative reconstruction and segmented vectorial reprojection calculation, wherein a scattered radiation correction and a radiation hardening correction are carried out in each iteration cycle for m≧2 different material components of the object being examined.

BRIEF DESCRIPTION OF THE DRAWINGS

The invention will be described in more detail hereinafter with reference to a further specification of the method steps using the figures, only the features required to understand the invention being illustrated and the following reference numerals being used: 1: CT system; 2: X-ray tube; 3: detector; 6: gantry housing; 7: patient; 7.1: soft tissue; 7.2 bone tissue; 8: patient couch; 9: system axis; 10: control and arithmetic-logic unit; 11: memory; 12: relationship between water layer thickness and ratio of scattered radiation to primary radiation; 13: characteristic of the primary radiation over the detector; 14: scattered radiation intensity profile at 70 kV with 20 cm water and subsequently 5 cm bone viewed in the direction of radiation; 15: scattered radiation intensity profile at 70 kV with 5 cm bone first of all and subsequently 20 cm water viewed in the direction of radiation; 16: scatter fraction characteristic at a radiation of 120 kVp and a bone density of 1.5 g/cm$^3$; 17: scatter fraction characteristic at a radiation of 70 kVp and a bone density of 1.5 g/cm$^3$; 18: scatter fraction characteristic at a radiation of 120 kVp and a bone density of 1.0 g/cm$^3$; 19: scatter fraction characteristic at a radiation of 70 kVp and a bone density of 1.0 g/cm$^3$; 20: scatter fraction characteristic for water without bone at 120 kVp; 21: scatter fraction characteristic for water without bone at 70 kVp; 22: measuring beam; 23: X-ray source; Prg$_1$-Prg$_n$: computer program.

In detail in the drawings.

DETAILED DESCRIPTION OF THE INVENTION

Figure 1:
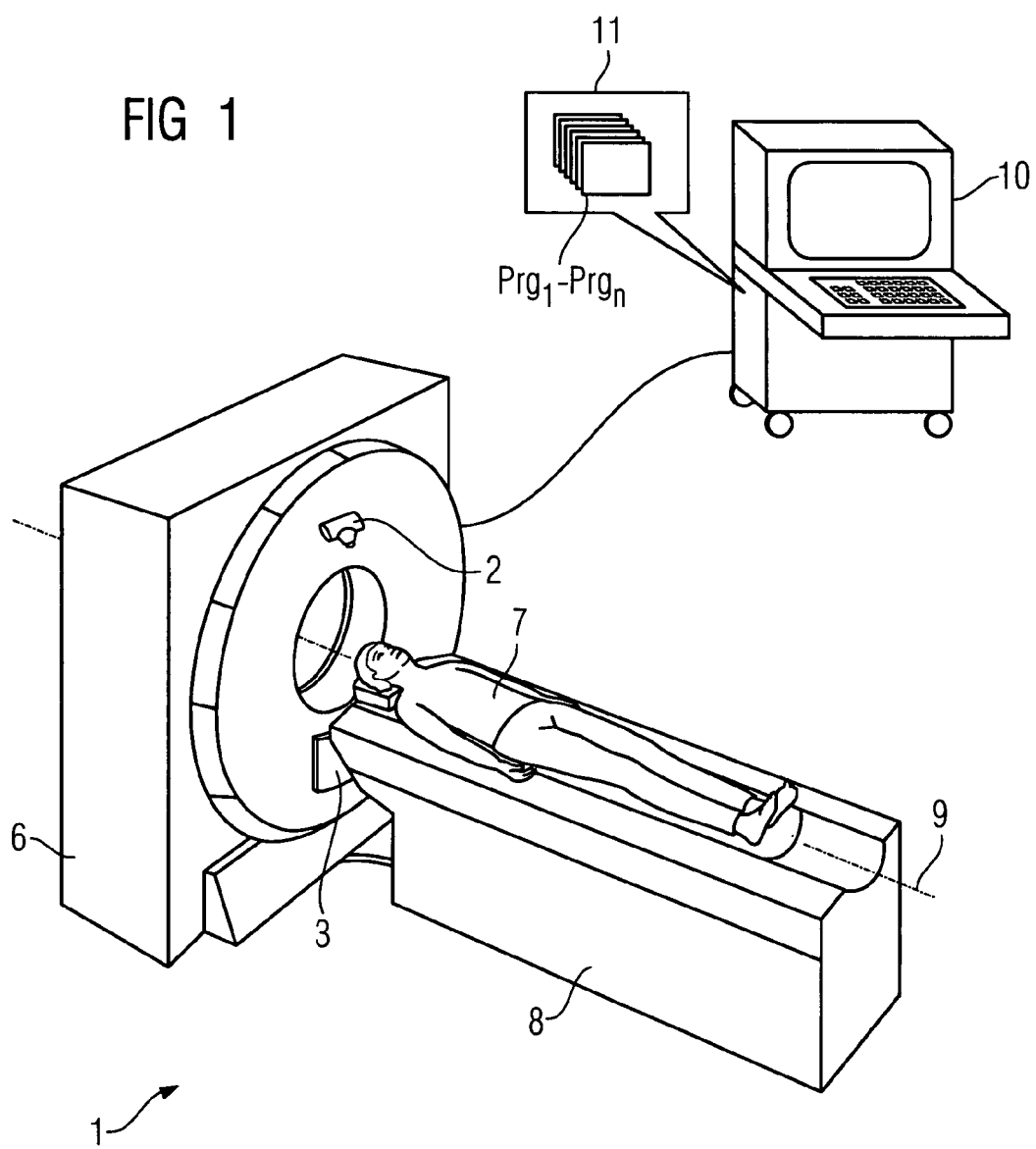
FIG. 1 shows a CT system with arithmetic-logic unit for carrying out the inventive method.

FIG. 1 shows an inventive CT system 1 with an X-ray tube 2 and an opposing multiline radiation detector 3. The two are mounted on a gantry (not visible here) in a gantry housing 6. For examination the patient 7 is pushed on a movable patient couch 8 along the system axis 9, through the opening between detector 3 and radiation source 2, while the radiation source 2 and detector 3 rotate around the system axis and scan the patient 7. The CT system 1 is controlled by a control and arithmetic-logic unit 10 which has a memory 11 in which computer programs Prg$_1$ to Prg$_n$ are stored which during operation assume control of the system and also execute the inventive method with respect to scattered radiation correction and hardening correction.

Figure 2:
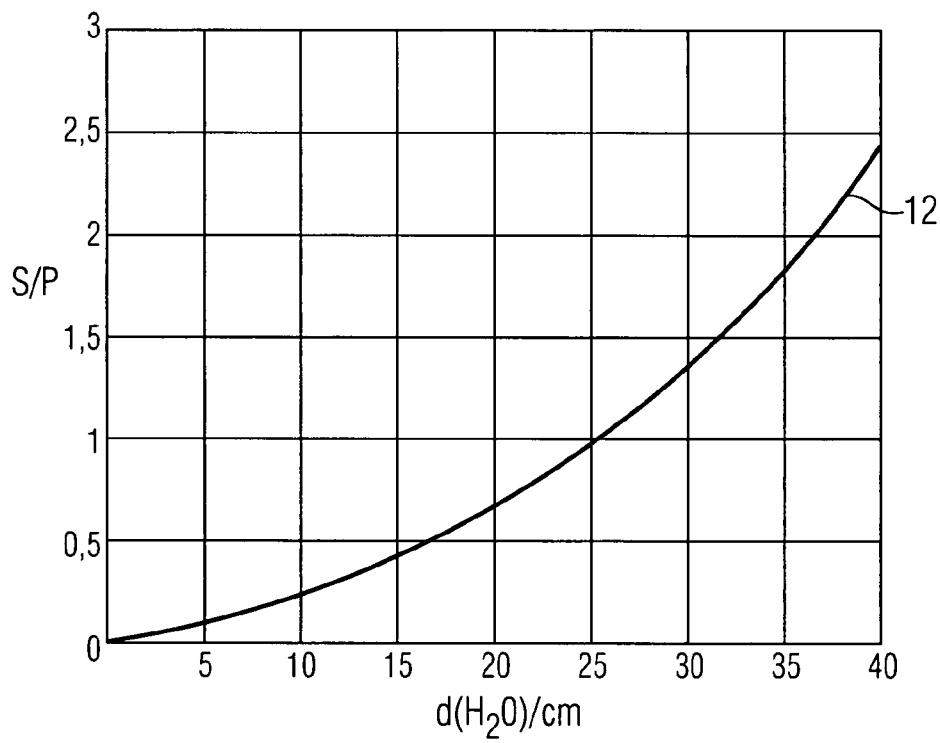
FIG. 2 shows a graph of the ratio of scattered radiation to primary radiation as a function of a penetrated water layer.

In FIG. 2 a water layer with a thickness dH$_2$O/cm and that has been penetrated by radiation is plotted on the abscissa and the curve 12 represents the relationship between this water layer thickness with irradiation by X-radiation with a beam potential of 120 kV in relation to the ratio, plotted on the ordinate, of scattered radiation to primary radiation S/P. As may be seen from this figure a ratio of 1 can be calculated even with a water thickness of about 25 cm.

Figure 3:
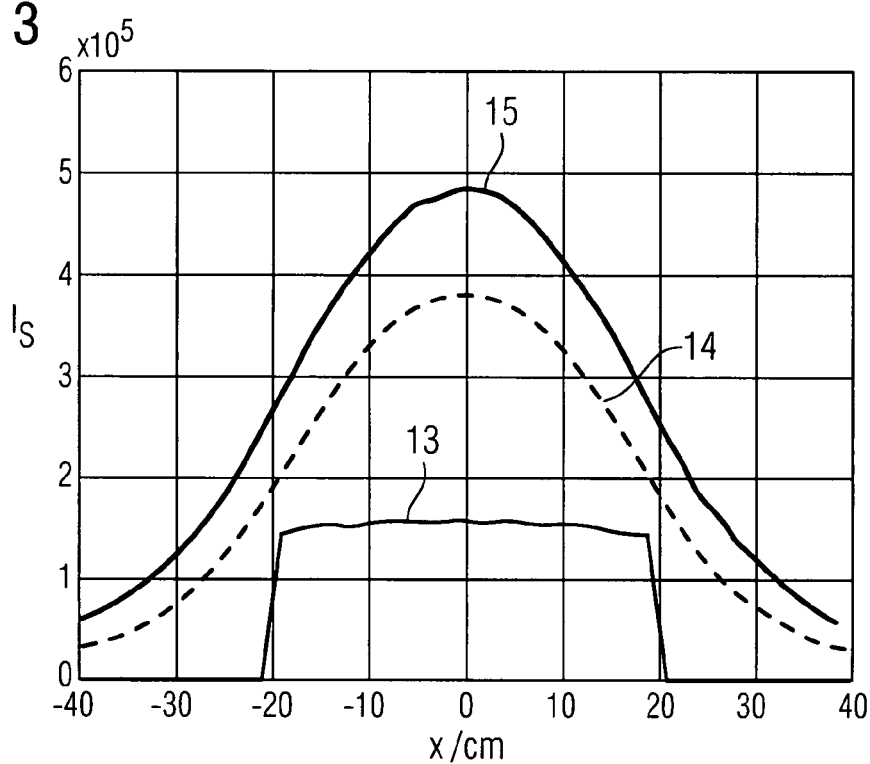
FIG. 3 shows an intensity profile of a primary radiation and the scattered radiation generated by two different layerings.

FIG. 3 shows the dependency of the scattered radiation on the material sequence, based on the two materials water and bone. The coordinate relative to a central detector line is indicated on the abscissa while the scattered radiation intensity I$_s$ is plotted on the ordinate in arbitrary units. The curve 13 shows the characteristic of the primary radiation over the detector which turns out to be almost trapezoidal. The curves 14 and 15 show the scattered radiation produced by the primary radiation, the curve 14 reproducing a scattered radiation intensity profile which corresponds first of all to 20 cm water and then 5 cm bone during irradiation with 70 kV X-radiation, while the curve 15 corresponds to the intensity profile of the scattered radiation during irradiation of first of all 5 cm bone and then 20 cm water.

The fundamental mathematical operators were generally formally stated in the introduction. The individual operations and variants thereof will be described in more detail hereinafter.

Figure 4:
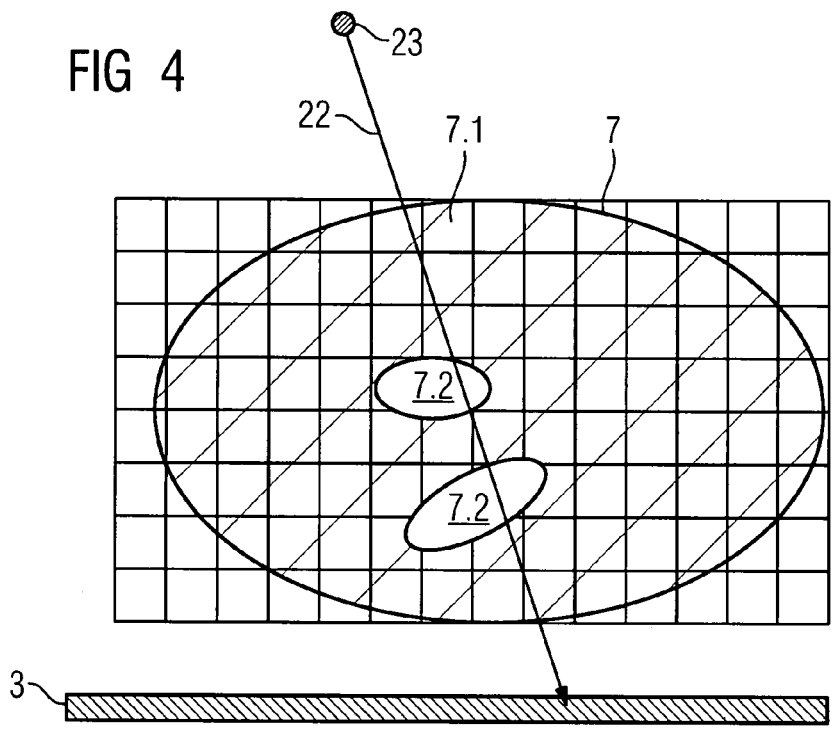
FIG. 4 shows a graph of the effect of different positioning of a bone layer in a water layer on the generated scattered radiation.

FIG. 4 schematically shows the inventive segmented, vectorized reprojection. The figure illustrates a measuring beam 22 which, issuing from an X-ray source 23, penetrates a patient 7 en route to a detector 3. On the one hand the patient has structures made of soft tissue 7.1 and structures made of bone tissue 7.2. The measuring beam 22 thus penetrates a large number of voxels which comprise different material components. These voxels are consecutively numbered in the beam direction and denoted by the subscript j. They have the following meanings:

$l_j$ = path length in voxel j, $L = (l_j)$ vector of path lengths in the voxels, $f_j$ = mean gray scale value in voxel j corresponding to the mean linear attenuation coefficient of the voxel, $T^{AW}$ = a threshold between air and water, $T^{WK}$ = a threshold between soft tissue and bone, $V^W$ = a "soft part vector", $V^K$ = a "bone vector".

The following relationships also apply:

$$v_j^K = \begin{cases} f_j/\alpha_K & ; \; f_j > T^{WK} \\ 0 & ; \; f_j \leq T^{WK} \end{cases}$$

and $$v_j^W = \begin{cases} f_j/\alpha_W & ; \; T^{AW} \leq f_j \leq T^{WK} \\ 0 & ; \; f_j < T^{AW} \text{ oder } f_j > T^{WK} \end{cases}$$

where $\alpha_w$ or $\alpha_K$ denote the mass attenuation coefficient in [cm$^2$/g] in the case of a specific reference energy of the radiation that is to be advantageously selected.

The soft part coverage and bone coverage in [g/cm$^2$] required for the hardening correction and the scattered radiation correction then results in:

$$b_W = \sum_j l_j v_j^W$$

and $$b_K = \sum_j l_j v_j^K$$

The vector $\underline{\lambda}$ generally represents a combination of three vectors $V^W$, $V^K$, L, where:

$$\underline{\lambda} = (V^W, V^K, L)$$

A single scalar variable can moreover be formed for example in the following way and is capable of at least sweepingly taking account of the dependency of the distribution of bone along the measuring beam relative to the distribution of soft tissue in the scattered radiation correction. The following variables are used for this purpose:

The voxel coordinates of the centre of the voxel j along the measuring beam where j=1 for designating the first voxel which belongs to the object, or of which the HU value corresponds to soft tissue or bone $$t_j = \sum_{j' < j} l_{j'} + l_j/2$$

Index sets of the "soft part voxel" or "bone voxel":

$$J^W = \{j | V_j^W > 0\}; \; J^K = \{j | V_j^K > 0\}$$

Focal points of the "soft part voxel" or "bone voxel" along the measuring beam:

$$\gamma_W = \frac{\sum_{j \in J^W} t_j v_j^W}{\sum_{j \in J^W} v_j^W}; \quad \gamma_K = \frac{\sum_{j \in J^K} t_j v_j^K}{\sum_{j \in J^K} v_j^K}$$

Length in soft part or in bone:

$$L_W = \sum_{j \in J^W} l_j; \quad L_K = \sum_{j \in J^K} l_j$$

The following scalar variable $\lambda$, which lies between $-\frac{1}{2}$ and $+\frac{1}{2}$, estimates the relative asymmetry in the distribution of the bone along the measuring beam compared with the soft part focal point:

$$\lambda = \frac{\gamma_W - \gamma_K}{L_W + L_K}$$

The following procedure is proposed by way of example for the two-component hardening correction:

Theoretically the following applies to the polychromatic projection data, which constitutes logarithmized, standardized primary intensities (=primary attenuations), at the spectrum Q(E) in the case of two radiologically different materials with the mass attenuation coefficients $\alpha_W(E) = (\mu_W/\rho_W)(E)$ and $\alpha_K(E) = (\mu_K/\rho_K)(E)$ as a function of the mass coverage densities $b_w$ or $b_K$ [g/cm$^2$] which penetrates the X-ray:

$$h(b_W, b_K) = \ln\left(\int_0^{eU} e^{-\alpha_W(E)b_W - \alpha_K(E)b_K} Q(E) dE\right)$$

The effective energy spectrum Q(E) of the radiation can be assumed to be known. Q(E) includes the emission spectrum of the X-ray tube, the effect of spectral filters and the energy-dependent detector response sensitivity. In other words, the function h(b$_W$, b$_K$) can basically be calculated in advance as a function of the mass coverage thickness (b$_W$, b$_K$) or it can be determined from experiments.

The two-component hardening vector accordingly consists in estimating from an existing, if still incorrect, CT (volumetric) image by segmented reprojection the two mass coverages $b_W$ and $b_K$ and then converting the existing polychromatic projection values into idealized monochromatic values for a reference energy Ê that is to be stipulated. The idealized monochromatic projection values are $$h^{mono}(b_W, b_K) = \alpha_W(\hat{E})b_W + \alpha_K(\hat{E})b_K$$

and the two-component hardening correction for a polychromatic projection value $\tilde{g}$ is then $$I(\tilde{g}; b_W, b_K) = \tilde{g} \cdot \frac{h^{mono}(b_W, b_K)}{h(b_W, b_K)}$$

Two-component estimation model for scattered radiation distribution:

By way of example a generalization of the "folding model" outlined in the already-cited document M. Zellerhof, B. Scholz, E.-P. Rührnschopf, T. Brunner: "Low contrast 3D reconstruction from C-arm data", Proceedings of SPIE. Medical Imaging 2005, vol. 5745, pp. 646 to 655 will be given below.

Even with the same attenuation of the X-radiation, i.e. with the same standardized primary intensity P of the radiation, the scattered radiation depends on the material composition and the sequence in the beam path. The information on two material components, usually water and bone, and their position can be considered in all methods considered here.

Since the scattered radiation distribution is relatively smooth, the estimation model can be reduced to a highly simplified pixel grid in order to reduce calculation complexity.

Semi-empirical folding model:

In the above-cited folding model the scattered radiation distribution is estimated using the following approaches:

$$S(x,y)=[pe^{-p}C(p)]**G(x,y)$$

wherein $$p(x,y)=-\ln(P(x,y))$$

where $P(x,y)$ is the estimation for standardized primary radiation distribution, and $G(x,y)$ is a two-dimensional folding core which empirically describes the low-pass filtering (smearing) caused by the scattered radiation propagation.

Alternatively the somewhat more generalized approach $$S(x,y)=[p^q e^{-p}C(p)]**G(x,y)$$

can be used, wherein the exponent q should be applied point-by-point to the function $p=p(x,y)$. As a rule $q>=1$ and can be empirically determined as a function of the mean path length, for example the mean of the variable $b_0(p)$ described below via the projection image. This more general approach corresponds to the first-mentioned approach when $q=1$. $C(p)$ is a "calibrating weighting function" where:

$$Ca(p)=C(b_0(p);U,F_{yz},a,\ldots).$$

This weighting function describes the ratio of scattered intensity to primary intensity S/P for standard bodies, for example homogeneous plates or elliptical cylinders, as a function of the layer thickness ($b_0(p)$) of water-equivalent material. This layer thickness can be clearly determined from the logarithmized primary attenuation $p=-\ln(P)$ based on the known hardening correction—a "water correction. C also depends on the following physical acquisition parameters: potential U, radiation filter, collimated field size $F_{yz}$ of the detector, scattered radiation grid, air gap a, etc.

C can in practice be calculated in advance by means of Monte Carlo calculations and be stored as a table or function. With fixed acquisition parameters C is only dependent on one variable, namely the water-equivalent layer thickness $b_0(p)$.

Using the weighting function C a simplified scattered radiation correction is obtained within the inventive iteration loop, a water-equivalent path length, derived from the estimated radiation attenuation and represented by P, and therefrom in turn a scatter fraction S/P via the tabulated weighting function C, being used and iteratively improved.

The proposed generalization lies in the weighting function C being dependent not only on a material variable, the water layer thickness, but having to be worked out from at least three variables $b_W$ and $b_K$ and $\lambda$. In the simplest case $\lambda$ is a parameter which describes the asymmetry of the position of the center of gravity of the bone compared with soft tissue in the beam path and the following applies:

$$C=C(b_W,b_K,\lambda;U,F_{yz},a,\ldots).$$

The current values of the two material thicknesses $b_W$ and $b_K$ and $\lambda$ are re-produced with each iteration step. These may then be used as new input values in the multi-parameter weighting table C to obtain an iteratively improved estimation of the scattered radiation.

Figure 5:
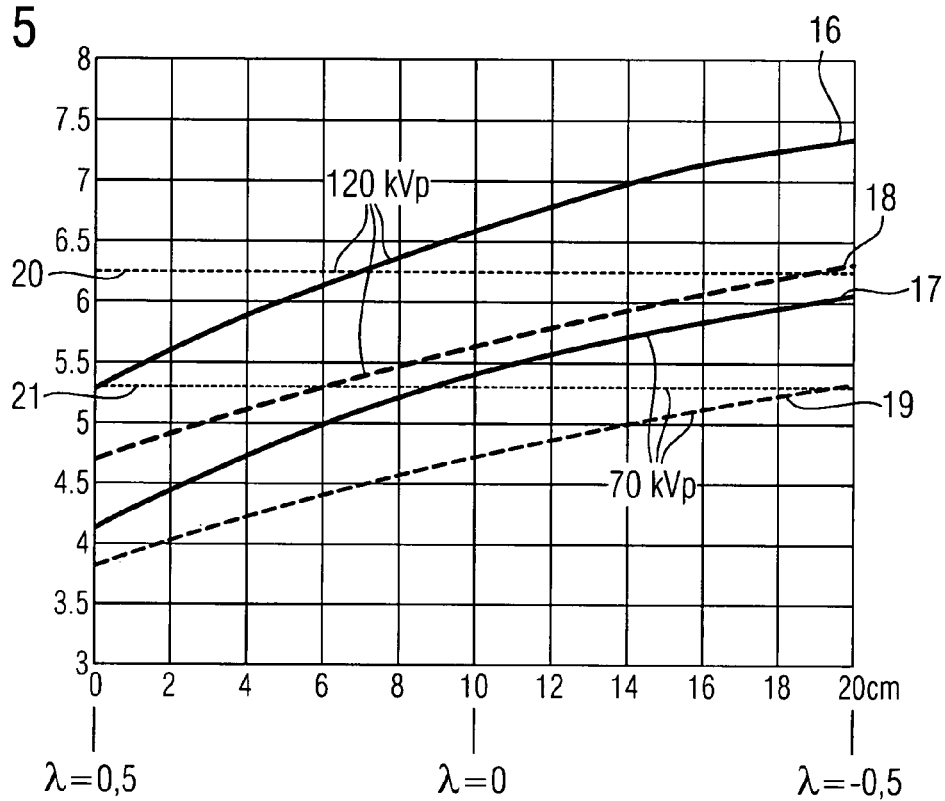
FIG. 5 shows a basic graph of the intensity profiles of a primary radiation and the scattered radiation generated by two different layerings.

FIG. 5 can be used to describe a simple linear application of the parameter $\lambda$. This figure shows the dependency of the scatter fraction S/P on the position of a bone layer 5 cm thick relative to a water layer 20 cm thick. The ratio of scattered radiation to primary radiation S/P is plotted on the ordinate and the spacing of the bone layer from the base of the entire layer of water and bone penetrated by radiation is plotted on the abscissa. The value $\lambda$ corresponding hereto is also plotted. The four curves 16 to 19 still differ in the X-ray spectra corresponding to the X-ray voltages of 70 kV and 120 kV and in the assumed bone density ($\rho_K=1.0$ or $1.5$ g/cm$^3$). The curve 16 corresponds to the scatter fraction characteristic at a radiation of 120 kVp and a bone density of 1.5 g/cm$^3$. The curve 17 corresponds to the scatter fraction characteristic at a radiation of 70 kVp and a bone density of 1.5 g/cm$^3$. The curve 18 corresponds to the scatter fraction characteristic at a radiation of 120 kVp and a bone density of 1.0 g/cm$^3$. The curve 19 corresponds to the scatter radiation characteristic at a radiation of 70 kVp and a bone density of 1.0 g/cm$^3$. The curves 20 and 21 show the corresponding values only for water without bone at 120 kVp and 70 kVp. The direction of irradiation is from above, i.e. with an abscissa value of 20 cm the bone layer is penetrated on top and is penetrated first by the radiation.

The curves 16 to 18 are slightly bent but for simplification interim values can be obtained in a first approximation by a linear interpolation. An improved approximation can in principle be achieved by parabolic or cubic interpolation.

If, for example, curve 17 is examined for 70 kV and $\rho_K=1.5$ g/cm$^3$, actual values of $L_K=5$ cm, $L_W=20$ cm and $b_K/L_K=\rho_K=1.5$ g/cm$^3$ result from segmented reprojection. For $-0.5<=\lambda<=0.5$ the scatter fraction S/P is then calculated by means of linear interpolation, so $s(\lambda)$ is designated $$s(\lambda)=s_m-\lambda(s_+ + -s_-),$$

wherein:

$s_+$=S/P for the extreme position of the bone close to the source in front of water where $\lambda=-0.5$, $s_-$=S/P for the extreme position of the bone close to the detector behind water where $\lambda=0.5$, and $s_m$=the mean $(s_+ + s_-)/2$.

If $b_K/L_K=\rho_K$ is neither 1.5 nor 1.0 g/cm$^3$ but lies therebetween, $s(\lambda)$ should be determined for $\rho_K=1.5$ and 1.5 g/cm$^3$ and then interpolated between the two results.

To cover the diversity of possible bone-water combinations, series of Monte Carlo calculations can be carried out in advance to determine and tabulate S/P at least for the extreme values of $s_+$ and $s_-$ for combinations of water and bone thicknesses ($L_W$, $L_K$) or, more generally, water and bone coverages ($b_W$, $b_K$).

Alternatively a Monte Carlo method or an analytical scatter model may be used. Basically it is also possible to directly calculate the scattered radiation distribution in each iteration step by a Monte Carlo method from the current voxeled volumetric image $f^{(n)}$. However the Monte Carlo simulation is still very time-consuming even with today's computers.

A further possibility is the deterministic or analytical calculation of scattered radiation of the first order from the current voxeled volumetric image $f^{(n)}$ by taking overall account of the contribution of higher scatter orders known from the document Y. Kyriakou, T. Riedel, W. A. Kalender: "Combining deterministic and Monte Carlo calculations for fast estimation of scatter intensities in CT", Phys. Med. Biol. 51 (2006), pp. 4567 to 4586. But this analytical method is also relatively complex since multi-dimensional integrals have to be numerically evaluated.

The scattered radiation correction algorithms $S_{corr}$ will be discussed hereinafter. These involve formulae (subtractive or multiplicative), as are mentioned for example in the document M. Zellerhof, B. Scholz, E.-P. Rührnschopf, T. Brunner: "Low contrast 3D reconstruction from C-arm data", Proceedings of SPIE. Medical Imaging 2005, vol. 5745, pp. 646 to 655.

The subtractive form consists in the subtraction of the estimated scattered radiation intensity from the respective uncorrected, standardized intensity distribution $I'(x,y)=I(x,y)/I_0$ where:

$P^{(n+1)}(x,y)=I'(x,y)-S^{(n)}(x,y)$, wherein (x,y) denote the pixel coordinates on the detector.

To avoid physically meaningless negative values a multiplicative scattered radiation correction can be used instead of the subtractive correction. The following applies in this connection:

$$P^{(n+1)}(x, y) = P^{(n)}(x, y)\frac{I'(x, y)}{P^{(n)}(x, y) + S^{(n)}(x, y)}.$$

For the event $S^{(n)}(x,y) \ll I'(x,y)$ the multiplicative correction changes to the subtractive correction.

Explicit reference is made to the fact that with the above-given illustration only a combination of two different material components, in this case soft tissue ($\equiv$water) and bone, have been explicitly disclosed without limiting the generality. However, the mathematical formulization readily allows a generalization to more than two components, for example soft tissue, bone and contrast medium. According to the invention a different number of components may also be used in the hardening correction and scattered radiation correction. However it is more advantageous with the hardening correction, which is a local effect, to take account of the larger number of different material components and their position than it is absolutely necessary with the scattered radiation correction, which is a far-reaching effect.

It is understood that the above-mentioned features of the invention can be used not only in the respectively given combinations but also in other combinations or alone without departing from the scope of the invention.

The invention claimed is:

1. A method for performing a bone hardening correction and a scattered radiation correction in X-ray computer tomography of a heterogeneous object with a CT system comprising an x-ray source and a flat detector, comprising:
   iteratively reconstructing a volumetric data of the object by an arithmetic-logic unit from a plurality of projection data of the object recoded by the CT system;
   iteratively reprojecting the volumetric data by the arithmetic-logic unit for soft tissue and bone in a vector; and
   iteratively performing the bone hardening correction and the scattered radiation correction during the reconstruction for at least two different material components of the object,
   wherein the iteration comprises steps of:
   starting the iteration by:
      determining a first standardized radiation distribution of a radiation striking the detector for a plurality of projection angles,
      calculating a first projection image from the first logarithmized radiation distribution for the plurality of projection angles,
      reconstructing a first volumetric image, and
   performing an iteration loop comprising steps of:
      segmenting a last-ascertained volumetric image into a plurality of material components of the object and determining a distribution of the material components on each measuring beam,
      estimating the scattered radiation correction by taking account of the distribution of the material components on all measuring beams,
      correcting a last-ascertained radiation distribution using the scattered radiation correction,
      calculating a scattered radiation-corrected projection image from the corrected last-ascertained radiation distribution,
      estimating the hardening correction by taking account of a fraction of material components penetrated on each measuring beam,
      correcting the scattered radiation-corrected projection images by a last-ascertained hardening correction,
      reconstructing a scatter and hardening corrected volumetric image,
   wherein the iteration is terminated or continued depending on a predetermined ascertained iteration condition.

2. The method as claimed in claim 1, wherein the object comprises two different material components.

3. The method as claimed in claim 2, wherein the object is a patient and the first material component is a soft tissue of the patient and the second material component is a bone tissue of the patient.

4. The method as claimed in claim 1, wherein the object comprises three different material components.

5. The method as claimed in claim 4, wherein the object is a patient and the first material component is air and the second material component is a soft tissue of the patient and the third material component is a bone tissue of the patient.

6. A method for performing a bone hardening correction and a scattered radiation correction in X-ray computer tomography of a heterogeneous object with a CT system comprising an x-ray source and a flat detector, comprising:
   iteratively reconstructing a volumetric data of the object by an arithmetic-logic unit from a plurality of projection data of the object recoded by the CT system;
   iteratively reprojecting the volumetric data by the arithmetic-logic unit for soft tissue and bone in a vector; and
   iteratively performing the bone hardening correction and the scattered radiation correction during the reconstruction for at least two different material components of the object, wherein the iteration comprises steps of:
starting the iteration by:
    determining a first standardized radiation distribution of a radiation striking the detector for a plurality of projection angles,
    calculating a first projection image from the first radiation logarithmized distribution for the plurality of projection angles,
    reconstructing a first volumetric image, and
performing an iteration loop comprising steps of:
    segmenting a last-ascertained volumetric image into a plurality of material components of the object and determining a distribution of the material components on each measuring beam,
    estimating a hardening correction by taking account of a fraction of material components penetrated on each measuring beam,
    correcting a last-obtained projection image by a last-ascertained hardening correction for a hardening corrected projection image,
    estimating a scattered radiation correction by taking account of the distribution of the material components on all measuring beams,
    correcting the hardening-corrected projection image using the scattered radiation correction,
    calculating a scattered radiation-corrected projection image,
    reconstructing a scatter and hardening corrected volumetric image,
wherein the iteration is terminated or continued depending on a predeteimined ascertained iteration condition.

7. An X-ray CT system, comprising
an X-ray source that emits X-ray beams to an object;
a flat detector that generates a detector data by measuring the X-ray beams penetrating the object and striking the detector; and
an arithmetic-logic unit that:
    iteratively reconstructs a volumetric data of the object from the detector data,
    iteratively reprojecting the volumetric data for soft tissue and bone in a vector, and
    iteratively performs a bone hardening correction and a scattered radiation correction during the reconstruction for at least two different material components of the object, wherein the iteration comprises steps of:
starting the iteration by:
    determining a first standardized radiation distribution of a radiation striking the detector for a plurality of projection angles,
    calculating a first projection image from the first logarithmized radiation distribution for the plurality of projection angles,
    reconstructing a first volumetric image, and
performing an iteration loop comprising steps of:
    segmenting a last-ascertained volumetric image into a plurality of material components of the object and determining a distribution of the material components on each measuring beam,
    estimating the scattered radiation correction by taking account of the distribution of the material components on all measuring beams,
    correcting a last-ascertained radiation distribution using the scattered radiation correction,
    calculating a scattered radiation-corrected projection image from the corrected last-ascertained radiation distribution,
    estimating the hardening correction by taking account of a fraction of material components penetrated on each measuring beam,
    correcting the scattered radiation-corrected projection images by a last-ascertained hardening correction,
    reconstructing a scatter and hardening corrected volumetric image,
wherein the iteration is terminated or continued depending on a predetermined ascertained iteration condition.

8. The X-ray CT system as claimed in claim 7, wherein the object comprises two different material components.

9. The X-ray CT system as claimed in claim 8, wherein the object is a patient and the first material component is a soft tissue of the patient and the second material component is a bone tissue of the patient.

10. The X-ray CT system as claimed in claim 7, wherein the object comprises three different material components.

11. The X-ray CT system as claimed in claim 10, wherein the object is a patient and the first material component is air and the second material component is a soft tissue of the patient and the third material component is a bone tissue of the patient.

* * * * *